(12) United States Patent
Mundschenk

(10) Patent No.: US 7,060,253 B1
(45) Date of Patent: Jun. 13, 2006

(54) TOPICAL FORMULATIONS AND DELIVERY SYSTEMS

(76) Inventor: David D. Mundschenk, 504 SE. Second Ave., Dania, FL (US) 33004

( * ) Notice: Subject to any disclaimer, the term of this patent is extended or adjusted under 35 U.S.C. 154(b) by 0 days.

(21) Appl. No.: 09/043,433

(22) PCT Filed: Sep. 20, 1996

(86) PCT No.: PCT/US96/15596

§ 371 (c)(1),
(2), (4) Date: Jan. 7, 1999

(87) PCT Pub. No.: WO97/10802

PCT Pub. Date: Mar. 27, 1997

(51) Int. Cl.
*A61L 9/04* (2006.01)

(52) U.S. Cl. .................. 424/45; 424/616; 514/945; 514/975

(58) Field of Classification Search .................. 424/45, 424/616; 514/945, 975
See application file for complete search history.

(56) References Cited

U.S. PATENT DOCUMENTS

| | | | |
|---|---|---|---|
| 3,976,223 A * | 8/1976 | Jass et al. | 424/45 |
| 4,338,564 A * | 7/1982 | Mundschenk et al. | |
| 4,657,758 A | 4/1987 | Goldemberg et al. | |
| 4,666,708 A | 5/1987 | Goldemberg et al. | |
| 4,687,663 A | 8/1987 | Schaeffer | |
| 4,964,539 A | 10/1990 | Mueller | |
| D315,496 S | 3/1991 | Pettengill | |
| 5,020,694 A | 6/1991 | Pettengill | |
| 5,038,963 A | 8/1991 | Pettengill et al. | |
| 5,059,417 A | 10/1991 | Williams et al. | |
| 5,084,268 A * | 1/1992 | Thaler | 424/45 |
| 5,104,644 A * | 4/1992 | Douglas | 424/45 |
| 5,145,684 A * | 9/1992 | Liversidge et al. | 424/489 |
| 5,174,990 A | 12/1992 | Douglas | |
| 5,208,010 A | 5/1993 | Thaler | |
| 5,225,183 A * | 7/1993 | Purewal et al. | 424/45 |
| 5,665,332 A * | 9/1997 | Mundschenk et al. | |
| 5,736,124 A * | 4/1998 | Akehurst et al. | 424/45 |

OTHER PUBLICATIONS

*CRC Handbook of Food, Drug and Cosmetic Excipients*, S. Smolinske, pp. 359-362 (1992).

P. Barkvoll. ("Should toothpastes foam? Sodium lauryl sulfate—a toothpaste detergent in focus", Noske Tannlaegeforenings Tidende 99(2)82-4 (1989)).

"Mouthwashes and Gargles", p. 1680, in American Hospital Formulary Services—Drug Information 1992, G. McEvoy et al. eds., American Society of Hospital Pharmacists).

Richard Russel, *A Dissertation on the use of Sea Water in the Diseases of the Glands: Particularly the Scurvy, Jaundice, King's Evil, Leprosy and the Glandular Consumption*, Preface (pp. i-xii), (1769).

Zinner. D.D., et. al.; Controlled Study of the Clinical Effectiveness of a New Oxygen Gel on Plaque. Oral Debris and Gingival inflammation, *Pharmacol. Ther. Dent.*, 1:7-15 (1970).

H. Mintzer, "Aerosols", Chapter 10 in *Pharmaceutical Dosage Forms—Disperse Systems*, Marcel Dekker, Inc. pp. 204-220 (1989).

D. Garlen, "Toothpastes", Chapter 14, in *Pharmaceutical Dosage Forms—Disperse Systems*, Marcel Dekker, Inc., pp. 511-532 (1989).

"Surfactants in Oral Hygiene Products", in *Surfactants in Cosmetics*, M. Reiger ed., Marcel Dekker, Inc, pp. 299-347 (1985).

* cited by examiner

*Primary Examiner*—Sreeni Padmanabhan
*Assistant Examiner*—Konata M. George
(74) *Attorney, Agent, or Firm*—Fredrikson & Byron P.A.

(57) ABSTRACT

A system for delivering a chemical agent in the form of a spray or foam, which in a preferred embodiment involves the use of an aerosol dispenser to deliver a formulation containing both an anionic surface active agent such as sodium lauryl sulfate as a foaming agent and a chemical agent such as either hydrogen peroxide as a disinfecting chemical agent or natural sea water.

16 Claims, No Drawings

TOPICAL FORMULATIONS AND DELIVERY SYSTEMS

CROSS REFERENCE TO RELATED APPLICATION

This application is filed under 37 USC 371 based on PCT Application No. PCT/US96/15596 filed Sep. 20, 1996.

TECHNICAL FIELD

The present invention relates to topical and other hygiene formulations, and to aerosol devices useful for the delivery of such formulations in the form of lathers and foams. In another aspect, the invention relates to formulations useful in the oral cavity, such as dentifrices containing hydrogen peroxide. In yet another aspect, the invention relates to the pharmacological use of surfactants such as anionic surfactants, and in particular sodium lauryl sulfate. In a further aspect the invention relates to topical and other hygiene formulations containing natural sea water.

BACKGROUND ART

Delivery Devices.

Formulations such as cosmetics and pharmaceuticals can be dispensed in a wide variety of vehicles and forms, including powders, capsules, liquids, aerosols, and the like. In particular, the delivery of formulations by the aerosol route is generally considered to take one of three forms: (1) the use of "space sprays", such as spray insecticides and air fresheners, which produce very fine sprays capable of evaporating rapidly or floating in the air; (2) the use of sprays such as hair sprays and deodorants, that are intended for continuous film formation; and (3) the use of aerated foams, such as shaving creams, which are produced by the rapid expansion of a propellant through an emulsion.

A variety of dispensers have been described for the purpose of delivering formulations of these various types. See, e.g., H. Mintzer, "Aerosols", Chapter 10 in *Pharmaceutical Dosage Forms-Disperse Systems*, Marcel Dekker, Inc. pp. 204–220 (1989). Aerosols for oral and nasal therapy are generally said to incorporate medicaments as solids suspended in a propellant. More recent advances in valve and propellant technology are said to provide improved delivery to the throat and nasal areas. Formulations delivered in aerosol form by the use of such devices can often include the use of surfactants. For instance, surfactants are commonly used in nebulizer vehicles to decrease surface tension and thus affect particle size (Mintzer, above, p. 206).

Yet other types of aerosol containers, pressurized with nitrogen, have been used to dispense toothpaste through a dip tube and foam-style valve. For a variety of reasons, however, such containers have not been commercially successful. See, e.g., D. Garlen, "Toothpastes", Chapter 14, pp. 511–532 in *Pharmaceutical Dosage Forms-Disperse Systems*, Marcel Dekker, Inc. 1989. As a result, various forms of "pump" dispensers have been developed for delivering toothpaste, the pumps relying on the use of a spring device to force the toothpaste out of a spout.

Surfactants

On a separate subject, a large number of surfactants, including sodium lauryl sulfate ("SLS"), have been widely used and found safe in a variety of cosmetic products, including dentifrices. See, e.g., "Surfactants in Oral Hygiene Products", pp. 299–347 in *Surfactants in Cosmetics*, M. Reiger ed., Marcel Dekker, Inc. 1985.

As of 1992, SLS itself was present in over 500 oral solid dosage forms approved by the FDA, as well as in 11 oral liquid dosage forms, 38 topical creams, lotions, ointments, medicates sponges or shampoos, and 28 dentrifices. *CRC Handbook of Food, Drug and Cosmetic Excipients*, S. Smolinske, pp. 359–362 (1992). The usefulness of sodium lauryl sulfate as a synthetic detergent in toothpaste has been studied in a recent article by P. Barkvoll. ("Should toothpastes foam? Sodium lauryl sulfate—a toothpaste detergent in focus", Norske Tannlaegeforenings Tidende 99(3)82–4 (1989)).

U.S. Pat. Nos. 4,657,758 and 4,666,708, for instance, describe dental rinses for loosening plaque and preventing plaque build-up. The rinses described in both patents rely on the detersive effect of oral surfactants. The '708 patent describes the use of SLS as one such oral surfactant, and further describes its function as a "potentiator" for other ingredients. In the Examples, patients were instructed to use one tablespoon of various rinses. Such rinse products, which are commercially available under the brand name "Plax", are typically swirled in the mouth in order to produce a weak foaming action.

Chemical Agents.

On yet another subject, there exist a number of useful chemical agents that, for one reason or another, have not previously been prepared in the form of a foamable composition, or delivered in the form of a foam or aerosol spray.

Natural sea water, for instance, has long been thought to provide certain desirable, including healing, qualities. See, for instance, Richard Russel, *A Dissertation on the use of Sea Water in the Diseases of the Glands: Particularly the Scurvy. Jaundice. King's Evil, Leprosy and the Glandular Consumption*, Preface (pages i–xii), (1769). Rarely, however, is sea water packaged and used for such purposes. This may be due to the present inability of the art to reproducibly prepare and package sea water in a stable form suitable for such use.

Hydrogen peroxide, for instance, is a common ingredient in mouthwashes and gargles. (See, e.g., "Mouthwashes and Gargles", p. 1680, in American Hospital Formulary Services—Drug Information 1992, G. McEvoy et al. eds., American Society of Hospital Pharmacists). Hydrogen peroxide functions as a weak antibacterial agent, a wound cleanser and a deodorant. It also serves a mechanical effect of effervescence and resultant removal of tissue and other debris.

When used as an oral topical, however, hydrogen peroxide is typically administered in the form of a concentrate, solution, or gel. The product is used for cleansing minor wounds, or minor gum inflammation resulting from dental procedures, orthodontic applications, denture irritations, accidental injury and other mouth and gum irritations (e.g., canker sores).

Such beneficial uses of hydrogen peroxide include its use as an oral germicide, cleansing agent and hemostat. It is considered a useful disinfectant for mucous membranes because of its low toxicity. See, e.g., Zinner. D. D., et. al.; Controlled Study of the Clinical Effectiveness of A New Oxygen Gel on Plaque. Oral Debris and Gingival inflammation, *Pharmacol. Ther. Dent.*, October 1970, 1:7–15.

Dental products such as "MentaDent", which was recently introduced by Chesebrough-Ponds, relies on the use of hydrogen peroxide. The commercial product identifies related U.S. Pat. Nos. 4,687,663, 4,964,539, 5,020,694, 5,038,963, 5,059,417, and Design patent No. D 315,496. Such patents relate variously to the use of a hydrogen peroxide component with a second component containing sodium bicarbonate; to a dentifrice composition containing, inter alia, hydrogen peroxide and a polyoxyethylene-polyoxypropylene copolymer; to multi-cavity or multi-chamber dispensing containers; and to a design for a dispensing container.

SLS and hydrogen peroxide have, on occasion, been used together in formulations for the oral cavity. See, for instance, U.S. Pat. Nos. 5,104,644 and 5,174,990 (mouthrinse), U.S. Pat. Nos. 5,084,268 and 5,208,010 (tooth whitening dentifrice).

An application previously filed naming the present inventor, and having U.S. Ser. No. 08/218,796, filed Mar. 28, 1994, discloses a system for delivering a chemical agent-containing formulation in the form of a foam, the system comprising a propellantless dispenser containing a foamable formulation comprising the chemical agent in the form of a solution or stable suspension and an aqueous solution of an anionic surface active agent as a foaming agent. Applicant has since found that such dispensers are less preferred, and in many cases unsuitable for such purposes, for a variety of reasons. These reasons include the fact that such dispensers are often subject to mechanical failure, particularly when subjected to agitation or external pressure changes, resulting in the production of inadequate foams.

As a result there continue to be few, if any, instances of the use of devices for the aerosol delivery of formulations to the oral cavity in the form of foams, particularly for formulations that incorporate hydrogen peroxide or sea water, or formulations for use in the oral cavity.

SUMMARY OF THE INVENTION

In one aspect, the present invention provides a system useful for delivering chemical agent-containing formulations in the form of foams or sprays. In particular, the invention provides a system for delivering a chemical agent-containing formulation in the form of a foam or spray, the system comprising an aerosol dispenser containing a formulation comprising the chemical agent in the form of a solution or stable suspension and an aqueous solution of an anionic surface active agent as a delivery agent.

In one preferred embodiment, the invention provides a system for delivering a foam or spray such as a disinfecting foam or spray, the system comprising an aerosol dispenser containing a deliverable (e.g., foamable or sprayable) formulation comprising lauryl sulfate, and preferably sodium lauryl sulfate, as a delivery agent. In a preferred embodiment, the system is used to deliver a cleansing, antiseptic, or disinfecting foam comprising hydrogen peroxide as the active agent. Such a system is particularly well suited for the delivery of hydrogen peroxide to the oral cavity, i.e., as a dental or oral formulation.

Applicant has found that the delivery of hydrogen peroxide to the oral cavity in the form of a foam or spray improves the effervescence of the formulation and, in turn, improves the removal of tissue and other debris. The formulation is particularly well suited to suspend and remove food particles and other debris, and then itself be rinsed away quickly. It does not appear that hydrogen peroxide has previously been effectively used for such purposes in the form of a foam or spray in the manner described herein, particularly in a manner suitable for commercial application.

The system of the present invention is capable of producing rapid detergent action in order to instantly provide voluminous quantities of microbubbles from relatively small initial volumes of formulation. This detergent action, in turn, greatly facilitates the effectiveness of the formulation as an oral rinse. The system of the present invention, for instance, can rapidly provide a volume of bubbles from about 2 grams of formulation that is as great or greater than the volume obtained by swirling up to an ounce (e.g., about 25–30 grams) of a product like Plax in the mouth for 30 seconds, as recommended by the manufacturer.

Formulations of the present invention having hydrogen peroxide have also been found to be particularly effective antifungal agents. To the best of Applicants' knowledge, hydrogen peroxide has not heretofore been approved or applied as an antifungal agent, and particularly not in the form of a foam or spray, or a composition delivered by an aerosol dispenser.

In another aspect, the present invention provides a method of delivering a formulation in the form of a organoleptically acceptable foam or spray, the preferred method comprising the steps of: (1) providing a formulation comprising a chemical agent to be delivered and sodium lauryl sulfate as a delivery agent, within an aerosol dispenser, and (2) delivering the formulation in the form of a foam or spray by activation of the dispenser.

In yet another aspect, the invention provides purified sea water compositions suitable for use in preparing formulations described herein. It appears that sea water has not heretofore been prepared in a form suitable for use in commercial cosmetic formulations.

DETAILED DESCRIPTION

The present invention provides a system for delivering a wide variety of chemical agents in the form of an efficacious foam. As used herein, the following words and terms shall have the meanings ascribed to them:

"system" will refer to an aerosol dispenser containing a formulation;

"formulation" will refer to a solution, e.g., as a single phase liquid or stable dispersion, which is capable of being delivered from an aerosol dispenser in the form of a foam or spray;

"chemical agent", in turn, will refer to the active agent or other agent to be delivered in the form of a foam;

"foam", and inflections thereof, when used as a verb shall refer to the ability of a formulation to form a foam when dispensed from an aerosol dispenser, and when used as a noun shall mean a liquid-film matrix with a mass of gas bubbles in it;

"spray", and inflections thereof, when used as a verb shall refer to the ability of a formulation to form a spray when dispensed from an aerosol dispenser, and when used as a noun shall mean a liquid moving in a mass of dispersed droplets, e.g., a fine jet of liquid discharged from a pressurized container, "delivery agent" shall refer to one or more ingredients in a formulation that functions to cause or facilitate either the foaming or spraying of the formulation when dispensed from an aerosol dispenser; and "dental formulation" shall refer to any formulation useful in or on the mouth or gums (such as dentifrice, mouthwash, gargle, dental liquid), or other nasopharyngeal application.

Preferred foams of the present invention are substantially stable, yet can be readily broken upon agitation. In other words, the foam is substantially stable after it is formed, so long as it is not agitated. An example of such a foam is one that can be dispensed into the palm of the hand and there remain for at least 30 seconds, and preferably for on the order of minutes, without collapsing. Once agitated however, for instance by rubbing the palms together, the foam is readily broken and in fact essentially disappears within a second or two. Preferred foams are similar in appearance and consistency to the suds obtained by the agitation of dishwashing liquids, that is, they are comprised of small bubbles.

While not intending to be bound by theory, it is believed that the unique combination of SLS as a delivery agent within an aerosol dispenser of the type described herein, together with chemical agents such as hydrogen peroxide, provide an optimal combination of such unexpected qualities as deliverability, foaming, effervescence, and cleaning ability.

Dispensers suitable for use in the system of the present invention are typically those that are capable of creating and dispensing a formulation in the form of a foam or spray in an aerosol manner through the use of a relatively low boiling liquid propellant such as butane and propane. The word "aerosol" will refer herein to the delivery of a foam or spray in a manner that employs a hydrocarbon or other suitable propellant, as further explained herein.

Aerosol dispensers are distinct from "propellantless" dispensers, the latter type being narrowly defined as those that avoid the use of a pressurized gas to achieve rapid expansion of a propellant through an emulsion. Propellantless dispensers are those that rely on the use of compressed air, for instance obtained by squeezing a bottle, as opposed to piston-type or spring-loaded dispensers.

In addition to a composition, a system of the present invention further comprises a dispenser, i.e., a container useful for holding one or more propellants, a valve, and an actuator. Those skilled in the are will be able to determine the manner in which the nature of these components can be selected and altered to determine such characteristics as delivery rate and uniformity, wetness and temperature of the foam or spray, foam or spray density, and the like.

Suitable aerosol dispensers provide an optimal combination of such properties as ease of use, capacity, inertness, safety and cost. Examples of suitable dispensers include those prepared of glass, plastic, metal or a combination of such materials. Glass containers must be carefully selected to provide an optimal level of pressure safety and impact resistance. Plastics may be employed to coat glass containers for improved safety, or to coat metal containers to improve corrosion resistance and enhance formulation stability.

The propellant supplies the necessary pressure within an aerosol system to expel the formulation from the container and, in combination with other components, to convert the formulation into the desired foam. Propellants may be broadly classified as liquified or compressed gases having vapor pressures generally exceeding atmospheric. Propellants within this definition include various hydrocarbons, especially fluoro-chloro-derivatives of methane and ethane, low molecular weight hydrocarbons such as the propanes, butanes and pentanes, and compressed gases such as carbon dioxide, nitrogen and nitrous oxide.

Preferred propellants suitable for use in the system of the present invention provide an optimal combination of such properties as compatibility and cost. Examples of preferred propellants include, but are not limited to, butane, dichlorodifluoromethane, dichlorotetrafluoroethane, isobutane, propane, trichloromonofluoromethane, and mixtures thereof.

Suitable propellants are commercially available from a number of sources, for instance, those identified as "Aeropres 46 (A-46)", a mixture of propane and isobutane available from Aeropres Corporation, Shreveport La.

Those skilled in the art, given the instant specification, will be able to identify and incorporate suitable valves and actuators for use in a system of the invention. The primary function of the valve is to regulate the flow of the formulation and propellant from the container. The characteristics of the delivered foam, including the accuracy and reproducibility of the delivery, should be optimized. Plastic, rubber, aluminum and stainless steel valves are particularly preferred.

An actuator is a fitting attached to an aerosol valve stem which, when depressed or moved, opens the valve to permit a foam or spray to issue from the container, and directs the foam or spray containing the formulation to the desired area. The actuator usually indicates the direction in which the formulation is dispensed and protects the hands or fingers from the refrigerant effects of the propellant. Actuators can incorporate an orifice of any suitable size and shape. Those skilled will appreciate the manner in which the orifice, the expansion chamber design, and the nature of the propellant and formulation can be adapted to modify the physical characteristics of the dispersed foam or spray.

A system of the present invention comprises a delivery agent, preferably selected from the class of surface active agents known as anionic detergents. Examples of suitable anionic delivery agents include sodium cocomonoglyceride sulfonate, sodium lauryl sarcosinate, sodium dodecyl benzenesulfonate, and miscellaneous other surfactants such as dioctyl sodium sulfosuccinate, sodium lauryl sulfoacetate, sulfolaurate, and the 2-hydroxyalkyl sulfates. See, e.g., "Surfactants in Oral Hygiene Products", pp. 299–347 in *Surfactants in Cosmetics*, M. Reiger ed., Marcel Dekker, Inc. 1985, the disclosure of which is incorporated herein by reference.

A particularly preferred delivery agent is SLS. SLS is itself classified as an emulsifying, wetting, and/or solubilizing agent. SLS is actually a mixture of sodium alkyl sulfates, primarily sodium lauryl sulfate containing not more than a total of 8% of sodium sulfate and sodium chloride. SLS is a long-chain fatty alcohol sulfate, and commercially available forms of SLS involve a mixture of long-chain saturated alkyl alcohols. Oral grades of SLS are generally made from naturally occurring fats and oils, mostly from coconut fatty acids, or the like. Some products are virtually all dodecyl derivative, while others contain mixtures of dodecyl, tetradecyl, and higher derivatives, depending on the degree of fractionation of the original fatty acids.

Such surface active agents, including SLS, are preferably present in the formulation at a final concentration of between about 0.05% and about 5%, and more preferably between about 0.1% and about 1%, by weight, based on the weight of the chemical agent formulation. Formulations containing less than about 0.5% SLS tend to have poor foaming characteristics, while those containing greater than about 5% SLS tend to impart unpleasant taste or other undesirable characteristics to the formulation.

The formulation delivered using a system of the present invention preferably comprises a chemical agent. Suitable chemical agents include any compound, solution or molecule that is desired to be delivered as a foam or spray to the body, including any cavity of the body. Examples of chemical agents that can be delivered to the body in the form of a foam or spray include topical analgesics, anesthetics, antibacterials, antibiotics, antifungal agents, anti-inflammatory agents (such as salicylates and steroids), antineoplastics, antiparasitics, antipruritics, antiviral agents, biologicals, contraceptives, dental preparations, deodorants, enzymes and digestants, germicides, hemorrhoidal preparations, hormones, minerals, vaginal preparations, and the like. Specific examples of preferred chemical agents include povidone iodine and hexachlorophene.

In a preferred embodiment, the system of the present invention is used for the preparation of foams for the application of abradants, antiacne preparations, antibacterials and/or antifungals, antidermatitis preparations, as well as antiherpes, anti-inflammatory, antiperspiration, antipuritics, antipsoriasis, antiseborrhea, or astringent agents, coal tar, depigmenting agents, detergents, emollients, fungicides, keratolytics, moisturizers, pediculicides, photosensitizers, scabicides, skin bleaches, skin protectants, cleansers, steroids, sulfur and salicylic acid, sun screens, vesicants, wart therapeutic agents, wound dressings, and the like.

Particularly preferred is a formulation that contains both hydrogen peroxide (as an anti-infective agent) and glycerin, aloe or other ingredient (as a skin or tissue protectant). The combination of hydrogen peroxide and glycerin has been used as effective local therapy for the treatment of pharyngitis, laryngitis, thrush, gingival infection and necrotizing ulcerative gingivitis. The combination, being non-toxic, has been found to be effective as a wide spectrum antibacterial and, as described herein, as an antifungal agent.

When used for treating oral bacterial infections, the combination provides relief from symptoms and serves as an adjunct to systemic therapy. It also relieves pain associated with these conditions, thereby enabling the patient to maintain or resume normal oral intake. The combination cleanses the tissue of debris, soothes irritated tissues and aids in restoring good oral hygiene. Patient acceptance has been good. See, for instance, Williams, J.C.; Topical Therapy in Infections of the Mouth and Pharynx, *Med Times,* 91:332–334 (1963).

Glycerin is quite effective in protecting the skin and buccal membranes of the mouth and oral cavity. FDA monographs, for instance, define glycerin as an "Active Skin Protectant" for use on skin, lips, and the oral cavity.

Similarly, hydrogen peroxide, for instance at a concentration of between about 1% and about 3% by weight, based on the weight of the formulation, is useful as a weak antibacterial agent, a wound cleanser (including suppurating ulcers and local infections), and a deodorant. When used in a dentifrice, hydrogen peroxide is useful for the removal of debris (by virtue of its effervescence) and in the treatment of pharyngitis and Vincent's stomatitis. Hydrogen peroxide is also useful as a disinfectant for cuts, burns, and the like, as well as for surfaces such as operating tables and instruments. Foams of the present invention provide a convenient, stable form of hydrogen peroxide, capable of providing a time release phenomenon upon breakdown of the foam structure.

Another preferred chemical agent is natural sea water. In stark contrast to the teachings of science and legend, Applicant has discovered a method in which natural sea water can be stabilized to allow it to be formulated into a product for topical application, e.g., incorporated as a "chemical agent" in a formulation of the present invention.

In a preferred embodiment natural sea water can be collected from any suitable source, preferably a well that provides a constant and convenient source. The water is then aerated and passed sequentially through a sequential series of pre-filters, e.g., gravel, sand, and finally activated carbon. After the optional pre-filter step(s) the water is finally passed through a suitable sub-micron (preferably 0.2 micron or less) filter. The resulting water surprisingly retains most, if not all, of the qualities desirable for cosmetic use, is stable upon prolonged storage, and can be used to provide stable effective formulations of the present invention.

Optionally, and preferably, one or more preservatives are added to the sub-micron filtered sea water in order to further lengthen its storage stability and preserve its utility. The identification of suitable preservatives will be well within the skill of those in the cosmetics arts, given the present disclosure. Preferred preservatives for sea water include those of the paraben series, and particularly methyl paraben and/or propyl paraben, which can be added to achieve final concentrations in the range of about 0.05% to about 0.5%, and preferably between about 0.1% and about 0.3%.

Commercial grade cosmetic and pharmaceutical preservative compositions are available, such as the liquid preservatives provided under the tradename "Phenonip" available from NIPA LABORATORIES, INC., Wilmington, Del. Phenonip preservative is described as a mixture of p-hydroxybenzoate esters (approximately 35% in combined weight) in 2-phenoxyethanol.

When prepared and used in the manner described herein, sea water provides a number of unexpected and desirable properties. When used as a chemical agent in a delivery formulation of the present invention, it is preferably used at a final concentration of between about 1% and about 10% by weight, and preferably between about 3% and about 5% by weight of the concentrate used to prepare the final formulation. It can serve, for instance, as a replacement for added salts in a formulation. In particular, it has been found that purified, stable sea water provides a useful thickening effect on foams. Those skilled in the art will appreciate the manner in which this effect can be controlled and used to one's advantage.

Systems of the present invention can be prepared in any suitable manner, using techniques and equipment within the skill of those in the art. See, e.g., D. Garlen, "Toothpastes", Chapter 14, pp. 511–532 in *Pharmaceutical Dosage Forms-Disperse Systems*, Marcel Dekker, Inc. 1989, the disclosure of which is incorporated herein by reference.

A preferred system as identified above can be prepared as follows:

(1) the desired ingredients are selected, based upon their known properties;

(2) the ingredients are mixed, together with adjuvants, according to methods within the skill of those in the art;

(3) the compatibilities of ingredients are evaluated for use in preparation and storage;

(4) the stability and potency of ingredients is assured; and (5) the resultant system is properly packaged and labeled for storage, transport, and use.

Formulations can be provided in either of two forms, either as a homogeneous prefabricated formulation that is already contained within an aerosol dispenser, or as a formulation that can optionally be modified (e.g., diluted) for use and added to an aerosol dispenser.

The final system can be prepared by any suitable means, including by either of two common approaches. In an approach known as the "cold fill" approach, the formulation (generally cooled to below 0 degrees C.) and the refrigerated propellant are measured into open containers (usually chilled). The valve-actuator assembly is then crimped onto the container to form a pressure-tight seal. During the period between propellant addition and crimping, sufficient volatilization of propellant occurs to displace air from the container.

In another approach, the "pressure fill" approach, the formulation is placed in the container and either the propellant is forced under pressure through the valve orifice after the valve is sealed, or the propellant is allowed to flow under the valve cap and then the valve assembly is sealed ("under the cap" filling). In both of these "pressure fill" cases, provisions must be made for the evacuation of air by means of vacuum or displacement with a small amount of propellant.

Other chemical agents and formulations useful with the system of the present invention can be prepared using a combination of commonly available ingredients identified as "generally recognized as safe" ("GRAS"). The dispenser can be filled and packaged using techniques within the skill of those in the art. For instance, a typical filling ratio is 60% product to 40% compressed air, according to FDA regulations. Special filling heads are used to fill and pressurize the system.

Examples of suitable chemical agents (and their intended use) include the following (percentages are provided on a weight basis, based on the weight of the final formulation):

essential oils, such as perfume oils, particularly in formulations in which the sodium lauryl sulfate serves the additional purpose of holding such oils in solution or stable suspension;

aloe vera (e.g., between about 0.1 and 10 g/100 ml formulation, and preferably between about 0.3 and 1 g/100 ml), used either with or without hydrogen peroxide;

sodium chloride (e.g., at physiological concentrations, generally about 0.9%), for use in treating cold sores and fever blisters and lesions associated with Herpes virus;

hydrogen peroxide (e.g., about 1% to about 15%, preferably about 8% to about 12%).

Suitable solvents for use in preparing a chemical agent solution of the present invention are those that provide an optimal combination of such properties as: the ability to solubilize the desired chemical agent; compatibility with the system; and suitability for topical use. An example of a particularly preferred solvent is purified water.

In a particularly preferred embodiment, other adjuvants such as fluoride, buffering agents, stabilizers and preservatives, foaming agents, antioxidants, flavorings, colors, viscosity modifiers, therapeutic additives, humectants, and binding agents can be used as well.

The system of the present invention is stable in storage, e.g., it can be stored one or more years without noticeable effect on its desired properties. It is preferably stored in a closed container and at room temperature.

In use, the system of the present invention provides a unique and desirable combination of such properties as ease of use, aesthetic appearance, formulation stability, uniform distribution of active ingredients, ease of spreading and penetration, and release and availability of medication on contact with dermatomucosal surfaces.

The system is well-suited for the delivery of formulations that have not previously been delivered in the form of foams, for instance, for the delivery of hydrogen peroxide to the oral cavity. When used for cleansing minor wounds or irritations of the mouth or gums, a small amount of the foam or spray is dispensed and applied to the affected area. It is allowed to remain in place for about 1 minute, and then expectorated. The foam or spray can be used up to 4 times daily (after meals and at bedtime) or as directed by a dentist of physician. Children younger than 12 years of age should be supervised by an adult in the use of the foam, and for children younger than 2 years of age, a dentist or physician should be consulted prior to use.

The system is particularly well suited for the delivery of formulations that are not generally delivered in the form of foams, including for the delivery of dentifrices, including dental liquids, mouthwashes, oral lavages and gargles that contain hydrogen peroxide.

The following Examples are given to illustrate, but not limit, the scope of this invention. Unless otherwise indicated, all percentages are by weight.

EXAMPLES

Example 1

3% Hydrogen Peroxide

A number of systems according to the present invention were prepared having the following ingredients:

| Concentrate I | 145 g |
| Propellant "A-46" | 25 g |

Concentrate I was prepared having the ingredients provided below:

| | Suitable range (%) | Concentrate I (%) |
|---|---|---|
| Deionized water | to 100 | to 100 |
| Hydrogen Peroxide | 3 | 3 |
| Aloe vera gel | 0–3 | 1 |
| Methyl paraben | 0.05–0.5 | 0.2 |
| Sodium lauryl sulfate | 0.2–3 | 1 |
| Fragrance | 0–1 | — |

The sodium lauryl sulfate was used as a delivery agent and hydrogen peroxide as a cleansing or antiseptic agent. The ingredients were mixed in a variety of relative concentrations and a dispenser was filled with the formulation. The system was used by actuating the valve in order to generate a foam from the nozzle. At optimal concentrations of ingredients a foam rapidly appeared in direct response to the pressure applied to the valve. The foam was a stable one, in that it remains on the skin with little visible shrinkage, yet it easily collapsed when rubbed between the fingers or palms.

The system is useful for a wide variety of applications, and particularly for applications in which the use of hydrogen peroxide is indicated and where the use of liquid hydrogen peroxide is inconvenient or ineffective.

Example 2

Body Foam with Sea Water

A number of systems according to the present invention were prepared having the following ingredients:

| Concentrate II | 145 g |
| Propellant A-46 | 25 g |

The concentrate was prepared having the ingredients provided below:

|  | Suitable range (%) | Concentrate II (%) |
|---|---|---|
| Sea water/Deionized water | to 100 | to 100 |
| Aloe vera gel | 0–3 | 1 |
| Methyl paraben | 0.05–0.5 | 1 |
| Sodium lauryl sulfate | 0.2–3 | 1 |
| Fragrance | 0–1 | — |

The sea water was filtered and preserved with (0.2%) methyl paraben in the manner described above, and used with deionized water in the ratio of 1 part sea water to 14 parts deionized water in order to provide an isosmotic formulation. In alternative embodiments, sea water and deionized water can be used at any suitable ratio, and preferably between the ratio of about 1 part sea water to 2 parts deionized water, and the ratio of about 1 part sea water to 30 parts deionized water.

The sodium lauryl sulfate was used as a delivery agent and the natural sea water was used for its purported healing effects. The ingredients were mixed in a variety of relative concentrations and dispensers were filled with the formulations using conventional techniques. The system was used by actuating the valve in order to generate a foam from the nozzle. At optimal concentrations of ingredients a foam rapidly appeared in direct response to the pressure applied to the valve. The foam was a stable one in that it with little visible shrinkage, yet it when rubbed between the fingers or palms.

The system is useful for a wide variety of applications, and particularly for applications in which the use of sea water is indicated and where the use of fresh sea water is inconvenient or ineffective.

Example 3

Foaming Skin Protectant/Tanning Accelerator with Sea Water

A number of systems according to the present invention were prepared having the following ingredients:

| Concentrate III | 70 g |
|---|---|
| Propellant A-46 | 25 g |

The concentrate was prepared in the order, and having the ingredients, provided below:

| Step | Ingredient (function(s)) | Concentrate III (approx. %) |
|---|---|---|
| 1. | Deionized water (solvent) | 62 |
|  | Sea water (solvent, chemical agent) | 4 |
|  | Aloe vera powder (skin conditioner) | 0.1 |
|  | Triethanolamine (pH adjuster) | 0.75 |
|  | Propylene glycol (solvent, humectant) | 3.7 |
|  | Glycerin (skin conditioning agent, humectant) | 3.2 |
| 2. | TEA lauryl sulfate (40.0%) (surfactant, emulsifying agent) | 1.8 |
| 3. | Mineral oil (skin conditioning agent, emollient) | 0.9 |
|  | Sorbitol (70.0%) (skin conditioning agent, humectant) | 1.7 |
|  | Shea butter (biological additive, skin conditioning agent) | 0.9 |
|  | Dimethicone (350) (skin conditioning agent) | 0.1 |

-continued

| Step | Ingredient (function(s)) | Concentrate III (approx. %) |
|---|---|---|
|  | Lauramide DEA (surfactant) | 0.9 |
|  | Stearic acid (surfactant, skin conditioning agent) | 8.7 |
|  | Polysorbate-60 (polyoxyethylene sorbitan monostearate (Tween 60) - surfactant, emulsifying agent) | 0.3 |
|  | Sorbitan stearate (surfactant, emulsifying agent) | 0.58 |
|  | Octyl methoxycinnamate (sunscreen) | 4 |
|  | Benzophenone-3 (sunscreen) | 2 |
|  | Octyl salicylate (sunscreen) | 3 |
| 4. | Germaben II-E (preservative) | 0.7 |
| 5. | Sodium silicate (buffering agent, corrosion inhibitor, pH adjuster) | 0.46 |

The ingredients were mixed in a variety of relative concentrations and a 2.5 ounce can dispenser was filled with the formulations. The system was used by actuating the valve in order to generate a foam from the nozzle. At optimal concentrations of ingredients a foam rapidly appeared in direct response to the pressure applied to the container.

The foam is formulated to be useful as a skin covering, to be rubbed over the entire hands to form a protective film—not unlike the protection afforded by a glove.

The system is useful for a wide variety of applications, and particularly for applications in which the use of sea water is indicated and where the use of fresh sea water is inconvenient or ineffective.

Example 4

Foaming Skin Protectant with Sea Water

A number of systems according to the present invention were prepared having the following ingredients:

| Concentrate IV | 145 g |
|---|---|
| Propellant A-46 | 25 g |

Concentrate IV was prepared having the same ingredients and concentrations as set forth above with respect to Concentrate III, although omitting the sunprotecting agents and using instead a total volume of 70% (rather than 62%) deionized water. Concentrate IV was used to fill 4.5 ounce can dispensers. Again, at optimal concentrations within the ranges set forth, the foamed formulation could be used by spreading it over the hands to provide a protective "glove-like" covering.

The present invention has been described with reference to various embodiments thereof. It will be apparent to those skilled in the art that many changes can be made in the embodiments described without departing from the scope of the present invention. Thus the scope of the present invention should not be limited to the formulations described in this application, but only by formulations described by the language of the claims and the equivalents of those formulations.

What is claimed is:

1. A system for delivering a chemical agent-containing formulation in the form of a spray or stable foam, the system comprising an aerosol dispenser containing a homogeneous stable aqueous formulation comprising the chemical agent in a solution or stable suspension and an anionic surface active agent as a delivery agent, the system having been prepared by a method that comprises forming the stable formulation and storing it as a single composition in the aerosol dispenser, wherein the surface active agent comprises sodium lauryl sulfate present at a concentration of between about 0.1% and about 1%, by weight, based on the weight of the formulation.

2. A system according to claim 1 wherein the formulation is an oral formulation.

3. A system for delivering a chemical agent-containing formulation in the form of a spray or stable foam, the system comprising an aerosol dispenser containing a homogeneous stable aqueous formulation comprising the chemical agent in a solution or stable suspension and an anionic surface active agent as a delivery agent, the system having been prepared by a method that comprises forming the stable formulation and storing it as a single composition in the aerosol dispenser, wherein the surface active agent comprises sodium lauryl sulfate, and the formulation comprises hydrogen peroxide as the chemical agent, and wherein the formulation further comprises glycerin.

4. A system for delivering a chemical agent-containing formulation in the form of a spray or stable foam, the system comprising an aerosol dispenser containing a homogeneous stable aqueous formulation comprising the chemical agent in a solution or stable suspension and an anionic surface active agent as a delivery agent, the system having been prepared by a method that comprises forming the stable formulation and storing it as a single composition in the aerosol dispenser, wherein the surface active agent comprises sodium lauryl sulfate, and the formulation comprises hydrogen peroxide as the chemical agent, and wherein the hydrogen peroxide is present at a concentration of between about 1% and about 3%, by weight, based on the weight of the formulation.

5. A method of delivering a chemical agent-containing formulation in the form of a spray or stable foam, the method comprising the steps of: (1) providing an aerosol dispenser containing a formulation comprising the chemical agent and an anionic surface active agent as a delivery agent, wherein the formulation and dispenser have themselves been provided by a method that comprises the steps of forming the stable formulation and storing it as a single composition in the aerosol dispenser, and (2) delivering the formulation in the form of a spray or stable foam by activation of the dispenser wherein the formulation comprises hydrogen peroxide as the chemical agent.

6. A method according to claim 5 wherein the surface active agent is selected from the group consisting of sodium lauryl sulfate, sodium cocomonoglyceride sulfonate, sodium lauryl sarcosinate, sodium dodecyl benzenesulfonate, dioctyl sodium sulfosuccinate, sodium lauryl sulfoacetate, sulfolaurate, and the 2-hydroxyalkyl sulfates.

7. A method according to claim 6 wherein the surface active agent comprises sodium lauryl sulfate.

8. A method according to claim 7 wherein sodium lauryl sulfate is present at a concentration of between about 0.1% and about 1%, by weight, based on the weight of the formulation.

9. A method according to claim 5 wherein the formulation is an oral formulation.

10. A method according to claim 5 wherein the formulation further comprises glycerin.

11. A method according to claim 5 wherein the hydrogen peroxide is present at a concentration of between about 1% and about 3%, by weight, based on the weight of the formulation.

12. A system for delivering a chemical agent-containing formulation in the form of a spray or stable foam, the system comprising an aerosol dispenser containing a homogeneous stable aqueous formulation comprising the chemical agent in a solution or stable suspension and an anionic surface active agent as a delivery agent, wherein the surface active agent is selected from the group consisting of sodium lauryl sulfate, sodium cocomonoglyceride sulfonate, sodium lauryl sarcosinate, sodium dodecyl benzenesulfonate, dioctyl sodium sulfosuccinate, sodium lauryl sulfoacetate, sulfolaurate, and the 2-hydroxyalkyl sulfates, and wherein the formulation is an oral formulation that comprises hydrogen peroxide as the chemical agent, wherein the hydrogen peroxide is present at a concentration of between about 1% and about 3%, by weight, based on the weight of the formulation.

13. A system according to claim 12 wherein the surface active agent comprises sodium lauryl sulfate at a concentration of between about 0.1% and about 1%, by weight, based on the weight of the formulation.

14. A method of delivering a chemical agent-containing formulation in the form of a spray or stable foam, the method comprising the steps of: (1) providing an aerosol dispenser containing a formulation comprising the chemical agent and an anionic surface active agent as a delivery agent, and (2) delivering the formulation in the form of a spray or stable foam by activation of the dispenser, wherein the surface active agent is selected from the group consisting of sodium lauryl sulfate, sodium cocomonoglyceride sulfonate, sodium lauryl sarcosinate, sodium dodecyl benzenesulfonate, dioctyl sodium sulfosuccinate, sodium lauryl sulfoacetate, sulfolaurate, and the 2-hydroxyalkyl sulfates, and wherein the formulation is an oral formulation that comprises hydrogen peroxide as the chemical agent.

15. A method according to claim 14 wherein the hydrogen peroxide is present at a concentration of between about 1% and about 3°%, by weight, based on the weight of the formulation.

16. A method according to claim 15 wherein the surface active agent comprises sodium lauryl sulfate at a concentration of between about 0.1% and about 1%, by weight, based on the weight of the formulation.

* * * * *